(12) United States Patent
Miller et al.

(10) Patent No.: US 9,730,615 B2
(45) Date of Patent: Aug. 15, 2017

(54) AUTOMATED SURFACE-BASED ANATOMICAL ANALYSIS BASED ON ATLAS-BASED SEGMENTATION OF MEDICAL IMAGING

(75) Inventors: Michael I. Miller, Towson, MD (US); Susumu Mori, Ellicott City, MD (US); Anqi Qiu, Singapore (SG)

(73) Assignee: THE JOHN HOPKINS UNIVERSITY, Baltimore, MD (US)

( * ) Notice: Subject to any disclaimer, the term of this patent is extended or adjusted under 35 U.S.C. 154(b) by 739 days.

(21) Appl. No.: 12/999,866

(22) PCT Filed: Jul. 7, 2009

(86) PCT No.: PCT/US2009/049819
§ 371 (c)(1),
(2), (4) Date: Dec. 17, 2010

(87) PCT Pub. No.: WO2010/005973
PCT Pub. Date: Jan. 14, 2010

(65) Prior Publication Data
US 2011/0092794 A1    Apr. 21, 2011

Related U.S. Application Data

(60) Provisional application No. 61/134,182, filed on Jul. 7, 2008.

(51) Int. Cl.
*A61B 5/00*    (2006.01)
*A61B 5/103*    (2006.01)
(Continued)

(52) U.S. Cl.
CPC .............. *A61B 5/103* (2013.01); *A61B 6/037* (2013.01); *G06T 7/0012* (2013.01); *G06T 7/46* (2017.01);
(Continued)

(58) Field of Classification Search
CPC ......... A61B 5/103; A61B 6/037; A61B 6/501; G06T 2207/10072; G06T 2207/20068;
(Continued)

(56) References Cited

U.S. PATENT DOCUMENTS 6,611,630 B1    8/2003  Miller et al.
6,633,686 B1    10/2003  Bakircioglu et al.
(Continued)

OTHER PUBLICATIONS

Qiu et al, Multi-structure network shape analysis via normal surface momentum maps, Neuroimage, vol. 42 issue 4(2008) 1430-1438.*
(Continued)

*Primary Examiner* — Ruth S Smith
(74) *Attorney, Agent, or Firm* — Venable LLP; Henry J. Daley (57) ABSTRACT

A non-invasive imaging system, including: a non-invasive imaging scanner; a signal processing unit in communication with the imaging scanner to receive an imaging signal from a subject under observation; and a data storage unit in communication with the signal processing unit, wherein the data storage unit stores template data corresponding to a tissue region of the subject, and wherein the signal processing unit is adapted to generate a surface map to encode a property of a subvolume of the tissue region using the template data.

27 Claims, 9 Drawing Sheets

(51) Int. Cl.
*A61B 6/03* (2006.01)
*G06T 7/00* (2017.01)
*G06T 7/46* (2017.01)
*A61B 6/00* (2006.01)

(52) U.S. Cl.
CPC ..... *A61B 6/501* (2013.01); *G06T 2207/10072* (2013.01); *G06T 2207/20068* (2013.01); *G06T 2207/20128* (2013.01); *G06T 2207/30096* (2013.01)

(58) Field of Classification Search
CPC . G06T 2207/20128; G06T 2207/30096; G06T 7/0012; G06T 7/46
See application file for complete search history.

(56) References Cited

U.S. PATENT DOCUMENTS

2007/0167699 A1    7/2007  Lathuiliere et al.
2008/0278804 A1*  11/2008  Gharib et al. ............... 359/462

OTHER PUBLICATIONS

International Search Report and Written Opinion, dated Feb. 4, 2010, issued in parent International Application No. PCT/US2009/049819.
Miller et al., "Geodesic Shooting for Computational Anatomy," J. Math. Imaging and Vision, vol. 24, pp. 209-228, 2006.

* cited by examiner

AUTOMATED SURFACE-BASED ANATOMICAL ANALYSIS BASED ON ATLAS-BASED SEGMENTATION OF MEDICAL IMAGING

CROSS-REFERENCE OF RELATED APPLICATION

This application is a U.S. national stage application under 35 U.S.C. §371 of PCT/US2009/0049819 filed Jul. 7, 2009, and claims priority to U.S. Provisional Application No. 61/134,182 filed Jul. 7, 2008, the entire contents of which are hereby incorporated by reference.

The U.S. Government has a paid-up license in this invention and the right in limited circumstances to require the patent owner to license others on reasonable terms as provided for by the terms of Grant No.: R01AG20012, P41RR15241, and RO1EB000975 awarded by the National Institutes of Health.

BACKGROUND

1. Field of Invention

The current invention relates to automated quantification of the anatomical images of tissue structures in a human or animal subject in a non-invasive manner.

2. Discussion of Related Art

Current radiological diagnosis is based on qualitative and subjective judgment. Even though quantitative analyses may significantly improve our ability to detect and characterize abnormality, currently there are essentially no quantitative techniques accepted as a part of routine radiological diagnosis. This is partly due to difficulties in analyzing tissues based on radiological imaging such as MR and CT images. This means, even a very basic image analysis such as the brain volume, can not be readily obtained quickly and automatically.

The principal limitation of the current state of the art is that in all anatomical representation there are as many unknowns to be estimated in the atlases as there are voxels— order 10-100 million. On the other hand, known representations of human anatomy at 1 mm scale reduce its relatively homogeneous substructures.

For automated image analysis, conventional voxel-based analyses have been widely used, in which the shape of each brain is transformed to that of a template brain. Once all brains are transformed (normalized) to the template, voxel-by-voxel analyses can be performed. In this type of analysis, each voxel is treated as an independent entity and no anatomical information is used during the process.

One shortcoming of the voxel-based analysis is that the result is not reliable for the brain areas where images do not provide contrasts. In other words, if there is an area with homogeneous intensity, registration results of such area are inherently mal-imposed. However, this reliability issue can not be appreciated from the results of voxel-based analysis results readily.

Characterizing disease is an area of growing importance. Existing morphometric shape analysis has largely focused on characterizing shape abnormalities associated with a disease via voxel based morphometry. More localized approaches have advantages of discovering regions that may be affected by diseases without the prior knowledge from pathological studies. Region of interest analysis in particular brain regions, such as the hippocampus and thalamus, has been used to overcome the mis-registration and has its own interest in associating the structure change with disease stages. However, there is considerable variation in shape change across multiple structures across disease populations. The assessment of the degree and pattern of structural changes in the multiple structures in circuits is necessary to optimally distinguish subjects with early forms of various diseases. As the growth of large available databases emerge, there are tremendous demands on automatic, sensitive, and reliable methods for localizing group differences in multiple structures in neuronal circuits and identifying morphometric biomarkers associated with a specific neuropsychiatric or degenerative disease. Region of interest analysis extended to multi-structure circuits of the brain can require the ability mediate between the 10,000,000 voxels and one single structure.

Another limitation of prior art include the noisy low-level voxel-based segmentation.

Thus, there is a need in the art for reducing the complexity associated with representing homogeneous substructures of a region, for example, a tissue region.

SUMMARY

Some embodiments of the current invention provides a non-invasive imaging system, including: a non-invasive imaging scanner; a signal processing unit in communication with the imaging scanner to receive an imaging signal from a subject under observation; and a data storage unit in communication with the signal processing unit, wherein the data storage unit stores template data corresponding to a tissue region of the subject, and wherein the signal processing unit is adapted to generate a surface map to encode a property of a subvolume of the tissue region using the template data.

Some embodiments of the current invention provides a workstation, comprising: a receiving engine to receive an imaging signal showing a tissue region from a subject and template data corresponding to the tissue region from at least one of a non-invasive imaging system, one or more data storage devices, a software simulation executed by one or more processors, or combinations thereof; and a processing engine to generate a surface map to encode a property of a subvolume of the tissue region in the imaging signal using the template data.

Some embodiments of the current invention provides a method of processing images, comprising: receiving template data corresponding to a region having a subvolume and an image showing the region; and generating a surface map to encode a property of the subvolume of the region using the template data.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1:
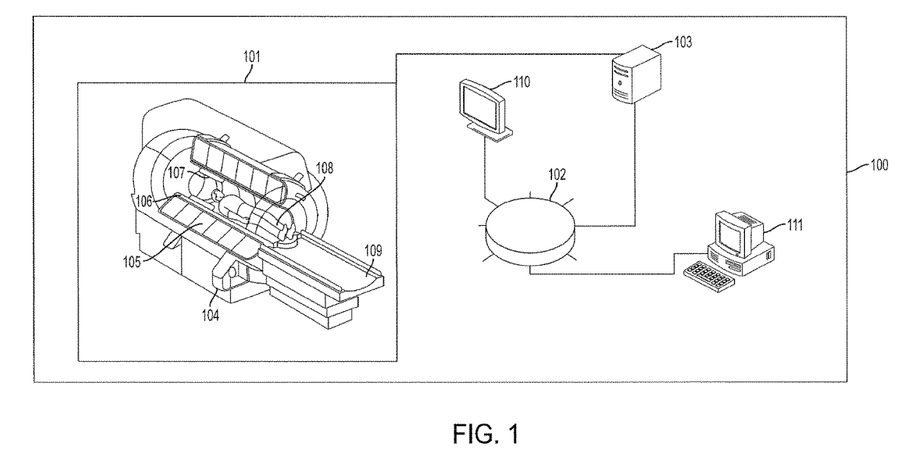
FIG. 1 is a schematic illustration of a non-invasive imaging system according to an embodiment of the current invention.

FIG. 1 is a schematic illustration of a non-invasive imaging system 100 according to some embodiments of the current invention. The non-invasive imaging system 100 includes an imaging scanner 101, a data storage unit 102, and a signal processing unit 103. Imaging scanner 101 may be, but is not limited to, a magnetic resonance imaging (MRI) scanner, a computed tomography (CT) scanner, a positron emission tomography (PET) scanner, a single positron emission computed tomography (SPECT) scanner, or combinations thereof. For example, an MRI scanner may have a base 104 to support a main magnet 105 (providing a substantially uniform main magnetic field $B_0$ for a subject 108 under observation on scanner bed 109), a gradient system 106 (providing a perturbation of the main magnetic field $B_0$ to encode spatial information of the constituent water molecules of subject 108 under observation), and a radio-frequency (RF) coil system 107 (transmitting electromagnetic waves and receiving magnetic resonance signals from subject 108).

Data storage unit 102 stores template data corresponding to a tissue region of subject 108 under observation. The tissue region may be, for example, a brain, a heart, a muscle, and other intended organ of subject 108. The term "template" used herein does not necessarily require an actual material object, such as a three dimensional material object. It will be used generally to also refer to data or information that represents a geometrical configuration. A template of the tissue region may be derived from, for example, a plurality of images from a subpopulation with similar characteristics to that of subject 108. The plurality of images may be, for example, MRI images, CT images, PET images, SPECT images, etc. For example, the images can come from the same age group as subject 108 in some applications. This is because each age range may have different tissue shapes and contrasts. For example, the human brain undergoes considerable shape and contrast changes during the first 24 months of age. During this period, templates should be created from infants within a small range of ages (e.g., 0-1 month, 1-2 months, 2-4 months, etc.). The brain also undergoes aging processes which become apparent after approximately age 60. Therefore specific templates may be required for an older subpopulation. Templates can be constructed to take into account variations between genders, races, health conditions, or other subpopulations based on the potential application. A template may incorporate information from images from at least one subject that is different from subject 108 under observation. A template may incorporate information from images from a previous scan of subject 108 under observation. For example, a template may be derived from images of a variety of different contrasts, each favorably delineating, for example, some substructures in the tissue region. For example, $T_1$-weighted magnetic resonance images suitable for the cortex and deep gray matter structures of the brain may be used. For example, $T_2$-weighted magnetic resonance images having higher contrasts for the ventricles of the brain may be used. For example, diffusion tensor images in which intra-white matter structures of the brain are best delineated may be used. The template may comprise shape information of the tissue region. The template may further incorporate variability information associated with registering the soft tissue region in the images from a subpopulation of subjects to the shape information. Registering a soft tissue region in an image from a subject to the shape information of a template may involve warping or transforming (e.g., translation, scaling, deforming, etc.) the soft tissue region in the image to align with the shape information of the template. Registering may also be referred to as normalizing. The term "template" include, but is not limited to these examples.

Data storage unit 102 may be, for example, a hard disk drive, a network area storage (NAS) device, a redundant array of independent disks (RAID), a flash drive, an optical disk, a magnetic tape, a magneto-optical disk, etc. However, the data storage unit 102 is not limited to these particular examples. It can include other existing or future developed data storage devices without departing from the scope of the current invention.

Signal processing unit 103 is in communication with imaging scanner 101 to receive imaging signals for forming images of subject 108. Signal processing unit 103 may be partially or totally incorporated within a structure housing imaging scanner 101. Signal processing unit 103 may be at least partially incorporated in a workstation that is structurally separate from and in communication with imaging scanner 101. Signal processing unit 103 may be incorporated in a workstation that is structurally separate from and in communication with imaging scanner 101. Signals received by signal processing unit 103 may be associated with, for example, a magnetic resonance contrast parameter, such as, for example, a relaxation time $T_1$, a relaxation time $T_2$, an apparent diffusion coefficient, a property associated with the blood oxygenation level dependent (BOLD) effect, a property associated with the diffusion tensor, etc.

Signal processing unit 103 is in communication with data storage unit 102. Signal processing unit 103 is adapted to generate a surface map that encodes a property of a subvolume of the tissue region in the imaging signal received from imaging scanner 101. The surface map may comprise a normal surface momentum map encoding a boundary shape of the substructure of the tissue region. The normal momentum map may be modeled as a linear combination of at least one spatially localizing function encoding spatial shape variation information of the subvolume of the tissue region. Signal processing unit 103 may be further adapted to compare the linear combination determined for the subvolume of the tissue region from the subject with a statistical database of the linear combination previously determined for the subvolume of the tissue region from one or more groups of subjects; and determine if said subject statistically belongs to said one or more groups of subjects. The linear combination may be further processed to extract a principal component. The generated surface map can be displayed on a viewing station 110 or a console station 111. The surface map may be used for further image analysis, classification, and disease diagnosis.

Viewing station 110 or a console station 111 may be, for example, a display device or a printing device. Example display devices may include, for example, a cathode ray tube (CRT), a light-emitting diode (LED) display, a liquid crystal display (LCD), a digital light projection (DLP) monitor, a vacuum florescent display (VFDs), a surface-conduction electron-emitter display (SED), a field emission display (FEDs), a liquid crystal on silicon (LCOS) display, etc. Example printing devices may include, for example, toner-based printers, liquid ink-jet printers, solid ink printers, dye-sublimation printers, and inkless printers such as thermal printers and ultraviolet (UV) printers, etc.

Figure 2A:
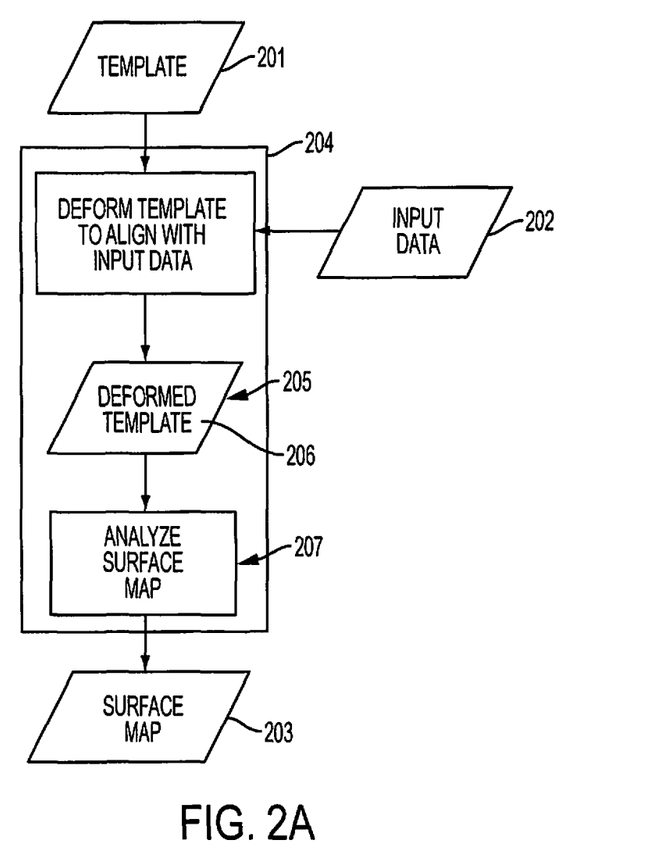
FIG. 2A shows a flow chart according to some embodiments of the current invention.

FIG. 2A shows a flow chart according to some embodiments of the current invention. Template 201 and input data 202 are inputs to block 204 which generates surface map 203 as an output. Template 201 corresponds to a region having at least one subvolume. Input data 202 may be, for example, an image showing the region. The image may be from a subject under observation. Template data 201 and input data 202 may be received from, for example, a non-invasive imaging system, one or more data storage devices, a software simulator executed by one or more processors, or combinations thereof. In block 205, template 201 is deformed to align with input data 202. The deformed template 206 is analyzed in block 207 to generate surface map 203.

Figure 2B:
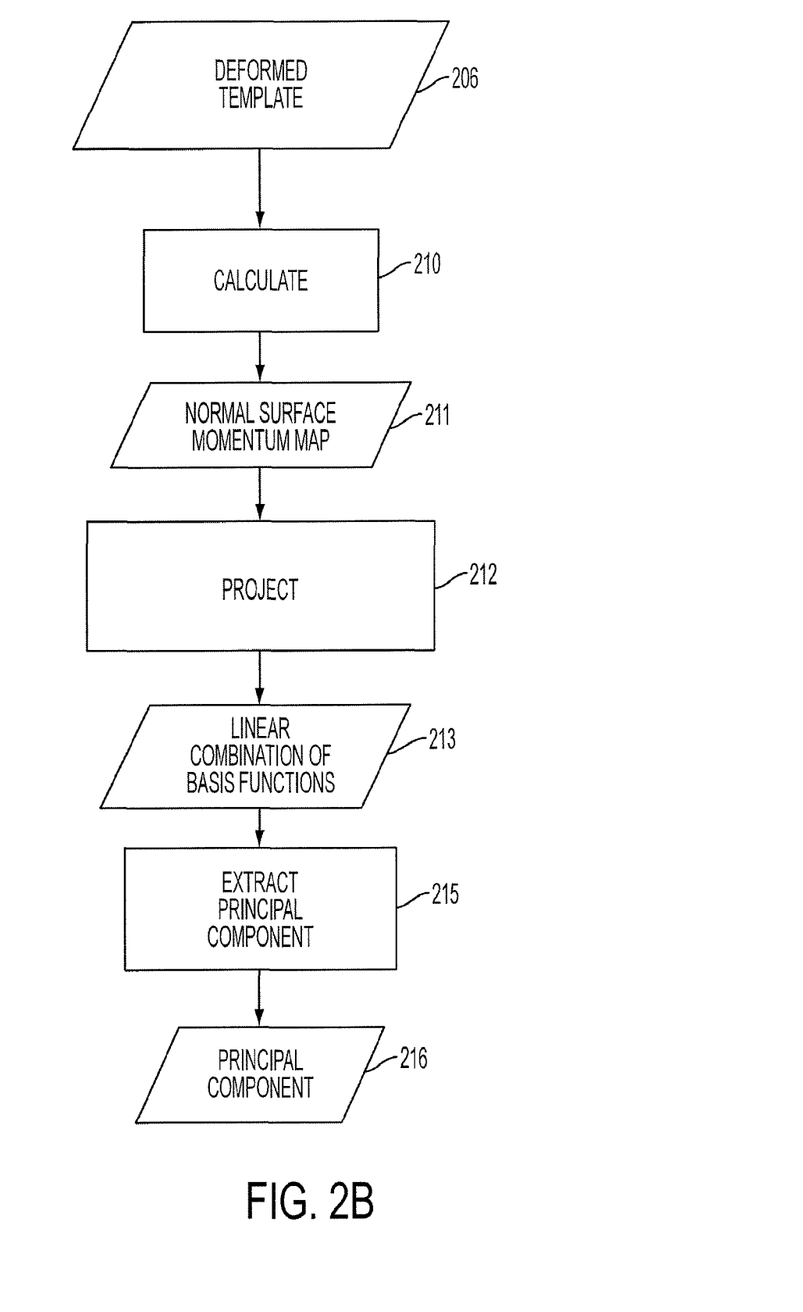
FIG. 2B shows another flow chart according to some embodiments of the current invention.

FIG. 2B shows another flow chart that describes example operations in block 207 according to some embodiments of the current invention. In block 210, calculations are performed on deformed template 206 to obtain normal surface momentum map 211. Normal surface momentum map 211 encodes a boundary shape of, for example, a subvolume of the region. In block 212, the normal surface momentum map 211 is projected to obtain a linear combination of at least one spatially localizing basis function encoding spatial shape variation information of the at least one subvolume of the region, as shown in block 213. In block 215, the linear combination is analyzed to extract a principal component 216 for each pixel in the normal momentum map 211.

Figure 3:
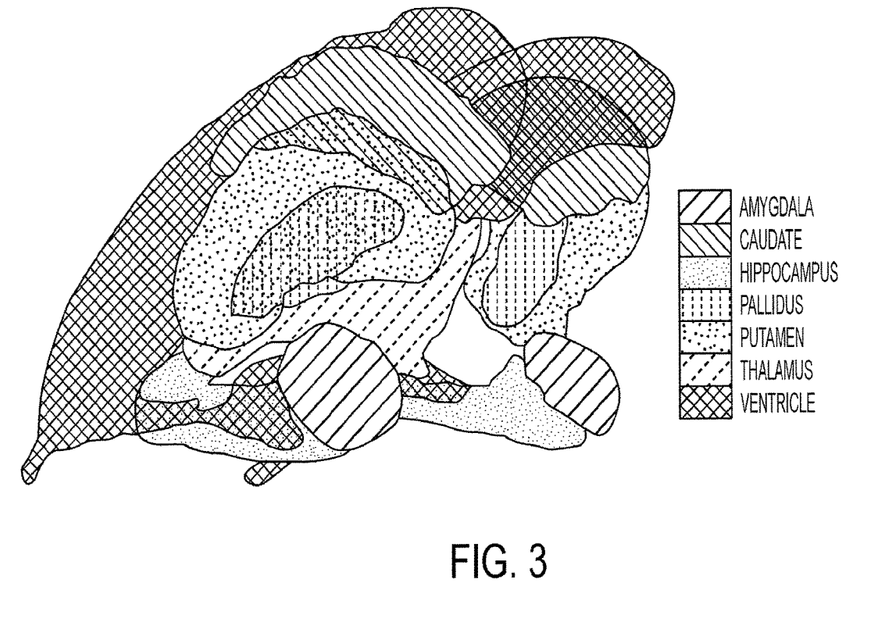
FIG. 3 illustrates homogeneous structures in a template represented by surface maps according to some embodiments of the current invention.
Figure 4A:
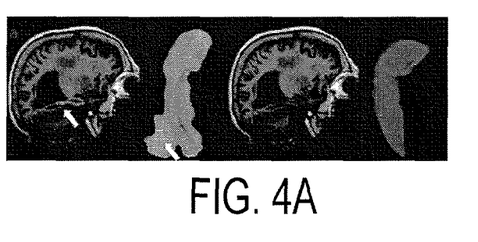
FIGS. 4A-4F show examples of filtering noisy voxel level statistics according to some embodiments of the current invention.
Figure 4B:
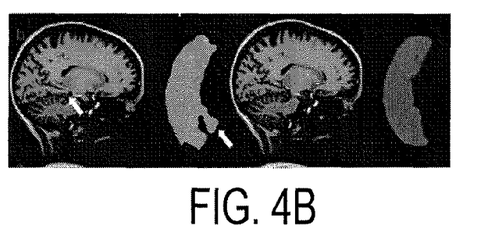
Figure 4C:
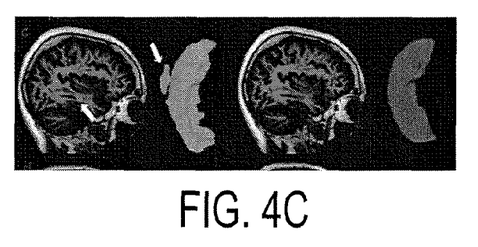
Figure 4D:
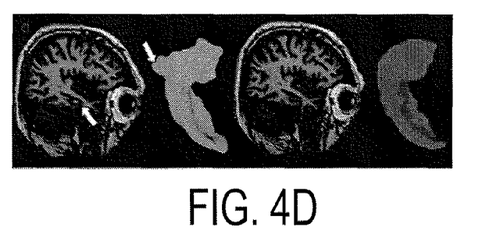
Figure 4E:
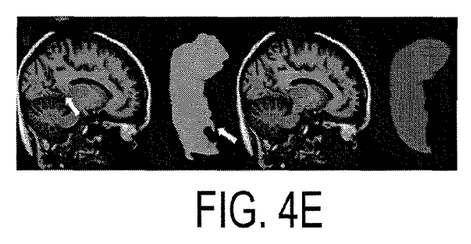
Figure 4F:
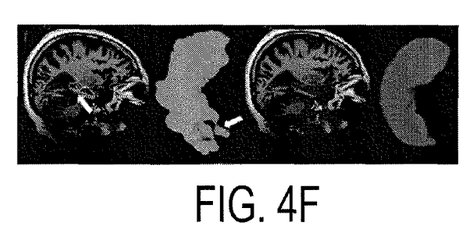

FIG. 3 shows an example MRI template in which shape information encoding the homogeneous structures of the region is reduced from about 10,000,000 voxels to about a few thousands by representing the homogeneous subvolumes as 2-dimensional (2-D) surface maps, instead of 3-dimensional (3-D) volumes.

FIGS. 4A-4F show examples of filtering noisy voxel level statistics according to some embodiments of the current invention. FIGS. 4A-4F each show one example of template injection for a hippocampus region. For each figure, the first (left-most) panel shows a sagittal slice of the hippocampus region with the cyan contour at the boundary of the hippocampus region automatically labeled by, for example, a software called FreeSurfer. The second panel shows the resulting surface representation. Arrows indicate where the errors occur in the FreeSurfer labeling process. The third panel of each figure illustrates the same sagittal slice with the pink contour at the boundary of the hippocampus after template injection that achieves segmentation denoising. The forth panel of each figure shows the corresponding surface representations after template injection.

FIGS. 4A-4F show an example using Large Deformation Diffeomorphic Mapping (LDDMM). The space of anatomical shapes $I \in \mathcal{I}$ may be modeled as an orbit of simple segmented subvolumes indexed over $x \in R^3$. The shapes of the subcortical nuclei are represented via their smooth connected subregions $\Omega^i \subset R^3, i=1, \ldots$ with associated smooth surface boundaries $S^i = \partial \Omega^i$, where i indexes structures. As will be seen, these smooth boundaries carry the shape information. The segmentations I are simple functions with value determined by the associated parcellations, for instance, $$I(x) = \text{amygdala}, x \in \Omega^{amygdala}, I(x) = \text{hippocampus}, x \in \Omega^{hippocampus} \ldots$$

To illustrate the template analysis of the population, the subcortical template depicted in FIGS. 4A-4F may be used. The template includes the lateral ventricles, amygdala, hippocampus, thalamus, caudate, putamen, and globus pallidus. The template may include a collection of homogeneous subvolumes and bounding smooth surfaces $\cup(I,S)$. The shapes and segmented imagery may be generated from each other via a flow of diffeomorphic solutions of ordinary differential equations $\dot{\phi}_t = v_t(\phi_t), t \in [0,1]$ starting from the identity map $\phi_0 = \text{id}$, and associated vector fields $v_t, t \in [0,1]$. To study shape properties of the targets $I \in \mathcal{I}$, the template can be injected into the target coordinates via diffeomorphic metric mapping which computes the geodesic connection $\phi_t \cdot I_{temp}, t \in [0,1]$ connecting the template $I_{temp}$ to the targets $I \in \mathcal{I}$. To ensure the curves are flows of diffeomorphisms, $v_t \in V$, a Hilbert space of smooth vector fields with kernel K and norm $\| \|_V$ may be used. The integrated norm $\|v_t\|_V, t \in [0,1]$ of the vector field generating the transformation is the geodesic length of the curve. In these smooth Hilbert spaces, a linear transformation of the vector field may be conveniently defined. This linear transformation is referred to as the "generalized momentum", determined via the kernel of the space $K: v_t \to M_t, =K^{-1} v_t$. $M_t$ is generalized momentum since $\|v_t\|_V^2 = \langle M_t, v_t \rangle$, which shows momentum acting against velocity as a generalization of energy. In interpreting these equations, it is noted that that generally the momentum is not a smooth function and must be interpreted as a distribution acting against smooth vector. The topological and global shape properties of the template of subcortical regions are injected by solving the LDDMM matching image that projects the template $I_{temp}$ into the target parcellations I. For this projection, a distance function $D(\phi_1 \cdot I_{temp}, I) = \|I_{temp} \circ \phi_1^{-1} - I\|^2$ between the deformed template, $I_{temp} \circ \phi_1^{-1}$ and targets, I may be defined. The template shapes in target coordinates are given by $\phi_1 \cdot (I,S)$ where the optimizing $\phi_1 = \int_0^1 \|v_t\|_V dt$ solves the following inexact matching problem:

$$J(v) = \int_0^1 \|v_t\|_V^2 dt + D(\phi_1 \cdot I_{temp}, I), \quad (1)$$

where $I_{temp}$ and I are respectively the template image and target image with a collections of subcortical structures, $i=1,2,\ldots n$ (n is the number of subvolume of structures). The mapped template segmentations are given by $\hat{I} = \phi_1 \cdot I_{temp}$; the shapes of the population of segmented targets are given by the injected surfaces inherited from the template under the mapping $S^i = \phi_1 \cdot S_{temp}^i, i=1, \ldots$. These are "filtered" or "denoised" approximations of the target parcellations. The shapes $S^i$ of the subcortical structures have statistics that will be discussed. The mappings in Equation (1) may be solved using the gradient descent algorithm according to $$M_t = |D\phi_{t,1}|(I \circ \phi_{t,1} - I_{temp} \circ \phi_t^{-1}) \nabla (I_{temp} \circ \phi_t^{-1}), \quad (2)$$

where $\phi_{t,1} = \phi_1 \circ \phi_t^{-1}$.

The subcortical structures are homogeneous subvolumes with shape encoded via the mappings applied to the collection of template surfaces and subvolumes. According to some embodiments of the current invention, the representation of shapes can be reduced to a representation of scalar fields concentrated on the boundary of the different homogeneous subvolumes. These scalar fields indexed over the bounding surfaces determine the "momentum" from the LDDMM mapped template surface shapes to target surface shapes in images from a population of subjects. The scalar fields may encode the spatial shape variation of the homogeneous subvolumes.

This parametric reduction follows from two key properties of the geodesic connection of the template surface shape to the target surface shape; (i) the conservation of momentum property, and (ii) the normality property.

Firstly, for example, the geodesic connection from the template surface shape to the target surface shapes is the minimum length curve carrying $\phi_1 \cdot I_{temp}$ inexactly to I satisfying:

$$\rho(I_{temp}, I)^2 = \inf_{\phi = \int_0^1 v_t(\phi_t)dt, \phi_0 = id} \int_0^1 (\|v_t\|_V^2 = \langle M_t, v_t \rangle) dt. \quad (3)$$

The Euler equation corresponding to the variational minimizing solution of Equation (3) specifies the geodesic shortest paths. The Euler equation may require that the geodesic shortest path be completely encoded by the initial momentum field $M_0$ rooted at the template at time 0 and conserved along the geodesic path according to:

$$M_t = |D\phi_t^{-1}|(D\phi_t^{-1})^* M_0 \circ \phi_t^{-1}, \quad (4)$$

where D is the Jacobian matrix of the transformation and * denotes matrix transpose. Thus, the problem of studying shapes of a population in a nonlinear diffeomorphic metric space becomes a problem of studying the initial momentum attached to the template in a linear space.

Secondly, the normality property of the geodesic follows from the fact that the geodesic the momentum is normal to the level lines of the template surface shape, as proven in Miller et al. (Miller, Trouve, Younes, Geodesic Shooting for Computational Anatomy, J. Math. Imaging and Vision, vol, 24, pp. 209-228, 2006) for the general case. As an example, the normality condition expressed by Equation (2) results in $M_0 = \mu \nabla I_{temp}$ following the gradient of the template with $\mu = |D\phi_1|(I \circ \phi_1 - I_{temp})$. This may be the essential basis for the parametric reduction that can be exploited for studying circuits of multiple structures which are homogeneous subvolumes. For homogeneous structures $\Omega$, such as, for example, the deep nuclei, the initial momentum is concentrated on the boundaries and normal to the bounding surfaces $S = \partial \Omega$. Parametrizing the momentum $M_0(\cdot)$ at time 0 thus becomes a representation of the boundaries of the substructures since the momentum is concentrated on the boundaries and is generated from a collection of normal vector fields which are solely supported on the boundaries of each of the subvolume structures. Hence, the momentum at time 0 may be modeled as $$M_0(x) = \mu(x)N(x), x \in S, \quad (5)$$

with $N(\cdot)$ being the normal field to the template surfaces. It is noted that $M_0(x)=0$ for $x \notin S = \partial \Omega$. Population shape variation may be represented by the signed-length of the scalar fields $\mu(x), x \in S$ with positive sign pointing outward motion and negative pointing inward motion relative to the template coordinates. $\mu(\cdot)$ may be referred to as a "normal surface momentum map" that encodes the shape change of subjects' subcortical structures relative to the template. The normal surface momentum map may be considered as a random momentum map when interpreted in statistical testing and empirical statistical model building.

To extract the normal scalar momentum maps encoding each subvolume $\mu^i(\cdot), i=1, \ldots$ of the template being aligned with target surfaces, for example, in the population of brain images, the template and target surfaces may be modeled as two-dimensional (2-D) smooth manifolds with the neighborhood of every point on the surface equivalent to a 2-D plane in the Euclidean space. Each plane can be uniquely defined by a point and a vector originated at this point and normal to the plane, thus representing the surfaces as triangulated meshes, LDDMM surface mapping may be applied to extract the momentum fields indexed over the template surface $S_{temp}$ which carries them onto the target surfaces S. The LDDMM surface mapping directly compares the normal vectors of the deformed template surface and the target surface in the distance function given by $$D(\phi \cdot S_{temp}, S) = \sum_{f,g} \eta_{\phi_1(c_f)} \cdot W(\phi(c(f)), \phi(c(g))) \eta_{\phi(c(g))} - \quad (6)$$
$$2 \sum_{f,q} \eta_{\phi(c_f)} \cdot W(\phi(c(f)), c(q)) \eta_{c(g)} + \sum_{q,r} \eta_{c_q} \cdot W(c(q), c(r)) \eta_{c(r)},$$

where the deformed template and target surfaces are represented by the center of face i, $c_i$, and the normal vector of face i, $\eta_{c_i}$. f,g are indices of the faces on the deformed template surface and q,r are indices of the faces on the target surfaces. W, a radial positive definite 3×3 diagonal matrix function, may serve as smoothing kernel. The terms in Equation (6) integrate local geometry for each face via inner products of its normal with normals of neighboring faces. The choice of kernel function W may determine the local neighborhoods used in the calculations. The first and last terms measure the local geometry within the deformed template surface and the target surfaces, respectively, and the middle term measures the mismatch in local geometry between the deformed template surface and the target surface.

Figure 5:
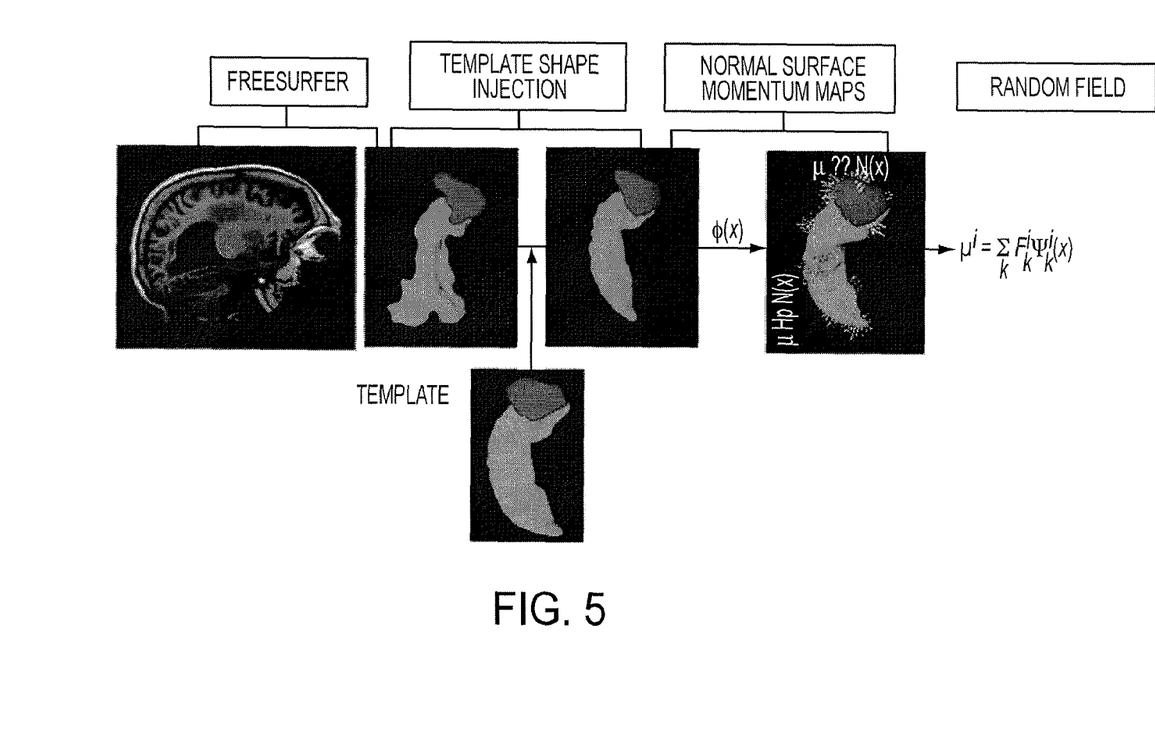
FIG. 5 depicts a pipeline showing the shape parametric reduction of the homogeneous structures according to some embodiments of the current invention.

FIG. 5 depicts a pipeline showing the shape parametric reduction of the homogeneous structures according to some embodiments of the current invention.

According to FIG. 5, shape information in the template 201 is injected into segmented images that are being obtained from, for example, Freesurfer via diffeomorphic mapping $\phi_1 : I_{temp} \rightarrow I$ to generate target shapes for each subject in a population being studied. Each target shape is generated according to $S^i = \phi_1 \cdot S_{temp}^i, i=1,2, \ldots, n$ (n is the number of subvolumes) as a momentum map. The momentum maps are indexed over the template coordinates $M_0^i = \mu^i N$ and are extracted by surface mapping $S_{temp}$ to $S^i$. FIG. 5 also shows an example normal surface momentum map generated according to some embodiments of the current invention. The example normal surface momentum map encodes the target shape with the associated normal momentum field.

The parametric shape is now encoded via the momentum maps. Each scalar momentum map $\mu^i(\cdot)$ on subvolume structure i may be assumed as a random field according to $$\mu^i(x) = \sum_k F_k^i \psi_k^i(x), x \in S_{temp}^i, \quad (7)$$

where the $F_k^i$ are random variables and $\psi_k^i(\cdot)$ are chosen as the k-th basis function of a complete set of orthonormal bases generated by, for example, the Laplace-Beltrami (LB) operator on template structure $S_{temp}^{i}$. The finite number of random variables, $F_k^i, K=1, \ldots$, characterizing the random momentum map $\mu^i(\cdot)$ of structure i may be determined by a goodness-of-fit at a certain discrepancy level.

The parametric dimension may then be reduced by one less dimension (dimension of the surface representations). Parametric reduction may be achieved via momentum map extraction in the population of target shapes using large deformation difformorphic metric mapping (LDDMM) for voxel and/or surface mapping.

The linear combination, for example, according to Equation (7), determined for a subvolume of the tissue region in an image from a subject may be compared with a statistical database of the same linear combination previously determined for the subvolume of the tissue region in existing images from one or more groups. Then, statistical correlation between the image from the subject and existing images from the one or more groups may be determined.

Figure 6:
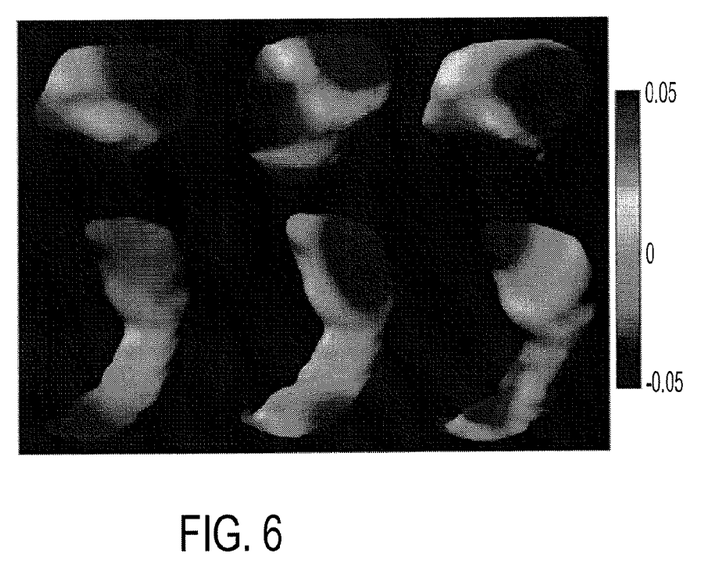
FIG. 6 shows example basis functions representing the spatial shape information in the template according to some embodiments of the current invention.

FIG. 6 shows example basis functions representing the spatial shape information in the template according to some embodiments of the current invention. The example basis functions shown are the Laplace-Beltrami basis functions defined on the amygdala (top row) and hippocampus (bottom row) of the brain. The right, middle, and left row show the second, fifth, and seventh LB basis functions, respectively.

To study the correlation in shape change within the subcortical network, the intercorrelation of $\mu^i(\cdot)$ across the multiple subcortical structures (e.g., hippocampus-amygdala circuit) may be calculated. $F_k^i$ from all structures, i=1, 2, ..., n (n is the number of subvolumes) may be assumed as Gaussian distributed with fixed mean and covariance. F denotes a feature vector in the form of $F=[F_1^1, F_2^2, \ldots, F_1^n, F_2^2, \ldots, F_1^n, F_2^n, \ldots]$. For example, principal component analysis (PCA) can be used to linearly project F to the orthogonal directions, $U_j, j=1,2, \ldots, m$, that carry the greatest variance according to $F=\Sigma_{j=1}^{m}\alpha_j U_j$. The orthogonal directions correspond to the principal components (PCs) that are ordered according to the amount of variance in the data which the PCs represent. The lower order PC-scores, $\alpha_j, j=1, 2, \ldots, m$, generally retain those characteristics of the shape which are not due to noise but are representative of average global shape properties. For example, for the brain region, the first set of PCs correspond to the subcortical structures such as, for example, caudate shape, putamen, thalamus, etc. The PC-scores are linearly independent variables. Each of the PC-scores may thus be tested using a linear regression model in which a diagnosis may be an independent variable and other factors may be dependent varibables (such as, for example, age, gender, and others including but not limited to total intracranial volume in the brain or heart volume in the heart, etc.).

The extracted PCs may be used for further analysis. For example, a first set of principal components may be extracted for the linear combination modeling a first set of normal surface momentum maps that encode a property of a subvolume of a region in a first plurality of images from a first plurality of subjects. A second set of principal components may be extracted for the linear combination modeling a second set of normal surface momentum maps that encode the property of the subvolume of the region in a second plurality of images from a second plurality of subjects. Then, a statistical difference between the extracted first and second set of principal components may be determined. The statistical difference signifies a physiological difference between said first and second plurality of subjects.

Figure 7:
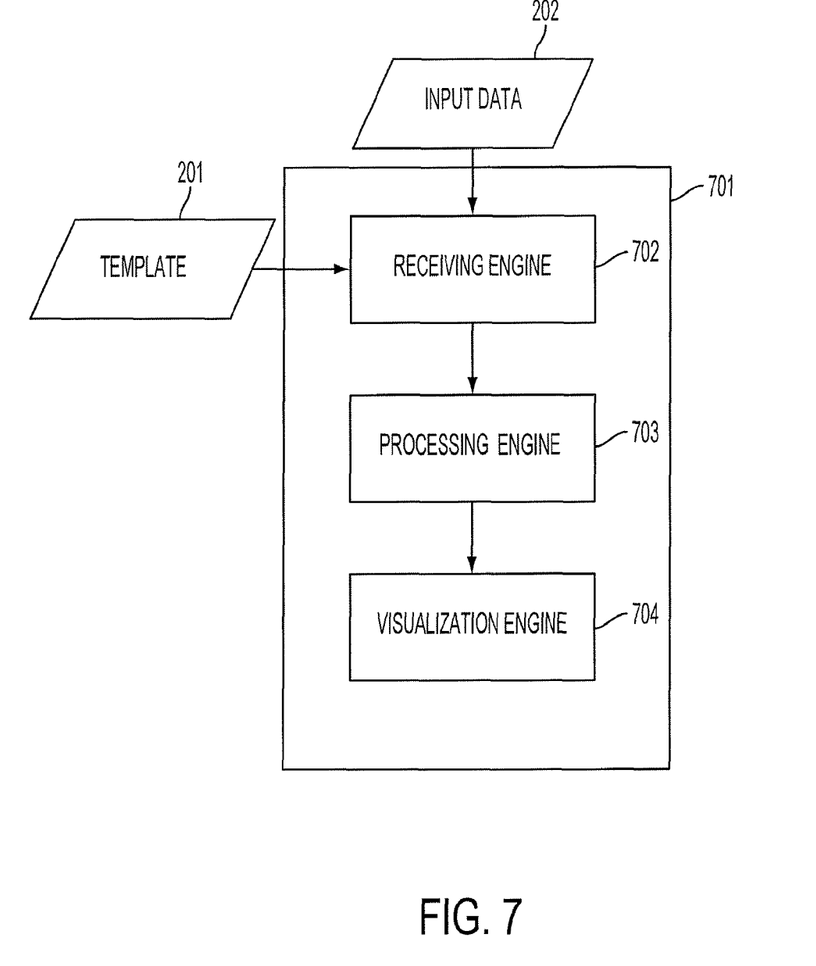
FIG. 7 shows a workstation according to some embodiments of the current invention.

Some embodiments of the current invention may include a computer-readable medium containing software, which software when executed by a computer, causes the computer to implement the method as discussed above. Example computer-readable medium may include, for example, CD-ROM, DVD, magneto-optical (MO) disk, hard disk, floppy disk, zip-disk, flash-drive, etc FIG. 7 is a schematic illustration of a workstation according an embodiment of the current invention. Workstation 701 may comprise receiving engine 702 and processing engine 703.

Receiving engine 702 may, for example, receive template 201 from, for example, data storage 108, and input data 206 from, for example, imaging system 100. The input date 202 may comprise a first and second plurality of images respectively from a first and second plurality of subjects.

Processing engine 703 may deform a template shape in template 201 to align the template shape with a subvolume of a tissue region in input data 202. Processing engine 703 may perform non-linear warping using, for example, large deformation difformorphic metric mapping (LDDMM). Processing engine 703 may further generate a surface map that encodes a property of a subvolume of the tissue region in input data 202 using template 201. The surface map may comprise a normal surface momentum map encoding a boundary shape of the substructure of the tissue region. The normal momentum map may be modeled as a linear combination of at least one spatially localizing function encoding spatial shape variation information of the substructure. The linear combination may be further processed to extract a principal component. The surface map may be used for further image analysis, classification, and disease diagnosis.

Processing engine 703 may further calculate a first and second set of surface maps, each encoding a property of the subvolume of the tissue region in input data 201. Input data 201 comprises a first and second set of images showing the tissue region from a first and second group of subjects, respectively. Processing engine 703 may further calculate a statistical difference between the first and second set of surface maps.

Workstation 701 may further comprise visualization engine 704 that displays the analyzed surface map, or the calculated statistic difference.

Workstations 701 may be a computer with at least one central processing unit (CPU) and a plurality of memories. Workstations 701 may also be a dedicated processing machine with such devices as, for example, a field programmable gated array (FPGA), a digital signal processing (DSP) chip, a graphic processing unit (GPU), an application specific integrated circuit (ASIC), etc.

Receiving engine 702, processing engine 703, and visualization engine 704 may be implemented by a computer with at least one central processing unit (CPU) and a plurality of memories. Receiving engine 702 and processing engine 703 may be implemented as, for example, a field programmable gated array (FPGA), a digital signal processing (DSP) chip, a graphic processing unit (GPU), an application specific integrated circuit (ASIC), etc. Visualization engine 704 may be, for example, a display device or a printing device. Example display devices may include, for example, a cathode ray tube (CRT), a light-emitting diode (LED) display, a liquid crystal display (LCD), a digital light projection (DLP) monitor, a vacuum florescent display (VFDs), a surface-conduction electron-emitter display (SED), a field emission display (FEDs), a liquid crystal on silicon (LCOS) display, etc. Example printing devices may include, for example, toner-based printers, liquid ink-jet printers, solid ink printers, dye-sublimation printers, and inkless printers such as thermal printers and ultraviolet (UV) printers, etc.

In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A non-invasive imaging system, comprising:
   a non-invasive imaging scanner; and
   a computer comprising:
      a signal processing unit in communication with said imaging scanner to receive imaging data of a tissue region from a subject under observation; and
      a data storage unit in communication with said signal processing unit, wherein said data storage unit stores template data corresponding to said tissue region of said subject, the template data of said subject comprising a plurality of template substructures,
   wherein said signal processing unit is adapted to:
      transform the template data to fit said plurality of template substructures to the imaging data through a shape transformation;
      calculate parameters of the shape transformation for at least one template substructure; and
      generate a surface map of said at least one of said template substructures based on said calculated parameters,
   wherein said surface map encodes a measure of shape differences between said template data and said tissue region.

2. The imaging system according to claim 1, further comprising:
   a display apparatus in communication with at least one of said signal processing unit and said data storage unit to display an analyzed deformation pattern.

3. The imaging system according to claim 1, wherein said surface map is modeled as a linear combination of at least one spatially localizing basis function encoding spatial shape variation information of a subvolume of said tissue region.

4. The imaging system according to claim 3, wherein said signal processing unit is further adapted to:
   extract a principal component of said linear combination of at least one spatially localizing basis function.

5. The imaging system according to claim 3, wherein said signal processing unit is further adapted to:
   compare said linear combination determined for said subvolume of said tissue region from said subject with a statistical database of said linear combination previously determined for said subvolume of said tissue region from one or more groups of subjects; and
   determine if said subject statistically belongs to said one or more groups of subjects.

6. The imaging system according to claim 1, wherein said imaging scanner is configured to scan the tissue region that is at least one of a brain, a heart, a liver, or other internal organ of said subject under observation.

7. The imaging system according to claim 1, wherein said data storage unit is configured to store said template data that incorporates at least one image from at least one subject that is different from said subject under observation.

8. The imaging system according to claim 1, wherein said data storage unit is configured to store said template data that incorporates at least one image from a previous scan of said subject under observation.

9. The imaging system according to claim 1, wherein said signal processing unit is at least partially incorporated in a workstation that is structurally separate and in communication with said imaging scanner.

10. The imaging system according to claim 1, wherein said signal processing unit is at least partially incorporated within a structure housing said imaging scanner.

11. The system of claim 1, wherein the shape transformation comprises a large deformation diffeomorphic metric mapping.

12. The system of claim 11, wherein the calculated parameters include momentum of the transformed template data.

13. The system of claim 12, wherein the surface map comprises a normal surface momentum map encoding a boundary shape based on the calculated momentum of the transformed template data.

14. The system of claim 12, wherein the calculated parameters are geodesic connection properties of the template data to the imaging data, the geodesic connection properties including a conservation of momentum property and a normality property.

15. A method of processing images on a computer, comprising:
   receiving imaging data of a tissue region of a subject under observation on a non-invasive imaging system;
   receiving template data corresponding to said tissue region of the subject under observation, the template data of said subject comprising a plurality of template substructures;
   transforming the template data to fit said plurality of template substructures to the imaging data through a shape transformation;
   calculating parameters of the shape transformation for at least one template substructure; and
   generating a surface map of said at least one of said substructures using the computer based on said calculated parameters,
   wherein said surface map encodes a measure of shape differences between said template data and said tissue region.

16. The method according to claim 15, wherein said template data is received from at least one of the non-invasive imaging system, one or more data storage devices, a software simulation executed by one or more processors, or combinations thereof.

17. The method according to claim 15, wherein said surface map is modeled as a linear combination of at least one spatially localizing basis function encoding spatial shape variation information of a subvolume of said tissue region.

18. The method according to claim 17, wherein said localizing basis function is a Laplace-Beltrami (LB) function.

19. The method according to claim 17, further comprising:
   comparing said linear combination determined for said subvolume of said tissue region in said imaging data from said subject with a statistical database of said linear combination previously determined for said subvolume of said tissue region in existing images from one or more groups; and determining if said imaging data is statistically correlated with said existing images from said one or more groups.

20. The method according to claim 17, further comprising:

extracting a principal component of said linear combination of at least one spatially localizing basis function.

21. The method according to claim 20, further comprising:

extracting a first set of principal components of said linear combination modeling a first set of normal surface momentum maps that encode said property of said subvolume of said tissue region in a first plurality of images from a first plurality of subjects;

extracting a second set of principal components of said linear combination modeling a second set of normal surface momentum maps that encode said property of said subvolume of said tissue region in a second plurality of images from a second plurality of subjects; and determining a statistical difference between the extracted first and second set of principal components.

22. The method according to claim 21, wherein determining said statistical difference comprises signifying a physiological difference between said first and second plurality of subjects.

23. The method of claim 15, wherein the shape transformation comprises a large deformation diffeomorphic metric mapping.

24. The method of claim 23, wherein the calculated parameters include momentum of the transformed template data.

25. The method of claim 24, wherein the surface map comprises a normal surface momentum map encoding a boundary shape based on the calculated momentum of the transformed template data.

26. The method of claim 24, wherein the calculated parameters are geodesic connection properties of the template data to the imaging data, the geodesic connection properties including a conservation of momentum property and a normality property.

27. A non-transitory computer-readable medium containing software, which software when executed by a computer, causes the computer to implement the method according to claim 15.

* * * * *

UNITED STATES PATENT AND TRADEMARK OFFICE
CERTIFICATE OF CORRECTION

| | |
|---|---|
| PATENT NO. | : 9,730,615 B2 |
| APPLICATION NO. | : 12/999866 |
| DATED | : August 15, 2017 |
| INVENTOR(S) | : Michael I. Miller et al. |

It is certified that error appears in the above-identified patent and that said Letters Patent is hereby corrected as shown below:

In the Specification

Column 1, replace paragraph 2 with the following paragraph:
This invention was made with government support under R01AG20012, P41RR15241, and RO1EB000975, awarded by the National Institutes of Health. The government has certain rights in the invention.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*